United States Patent [19]

Hoffmann et al.

[11] 4,176,181
[45] Nov. 27, 1979

[54] COMBATING PESTS WITH N-(AMINOMETHYLENE)-(MONOTHIO AND DITHIO)-PHOSPHORIC ACID DIESTER-AMIDES

[75] Inventors: Hellmut Hoffmann, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 931,046

[22] Filed: Aug. 4, 1978

[30] Foreign Application Priority Data

Aug. 19, 1977 [DE] Fed. Rep. of Germany ....... 2737403

[51] Int. Cl.² .................. A01N 9/36; C07F 9/24
[52] U.S. Cl. ........................... 424/211; 260/944
[58] Field of Search ................ 260/944; 424/211

[56] References Cited

U.S. PATENT DOCUMENTS 3,826,830  7/1974  Pallos ..................... 260/944 X

FOREIGN PATENT DOCUMENTS 225879  1/1970  U.S.S.R. .................... 260/944

*Primary Examiner*—Anton H. Sutto
*Attorney, Agent, or Firm*—Sprung, Felfe, Horn, Lynch & Kramer

[57] ABSTRACT

N-(Aminomethylene)-(monothio and dithio)-phosphoric acid diester-amides of the formula

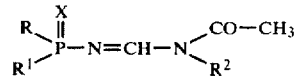

wherein
R and $R^1$ each independently is alkoxy or alkylthio,
$R^2$ is alkyl, and
X is oxygen or sulphur, which possess arthropodicidal and nematicidal properties.

10 Claims, No Drawings

COMBATING PESTS WITH N-(AMINOMETHYLENE)-(MONOTHIO AND DITHIO)-PHOSPHORIC ACID DIESTER-AMIDES

The present invention relates to and has for its objects the provision of particular new N-(aminomethylene)-(monothio and dithio)-phosphoric acid diester-amides which possess pesticidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is already known that O,S-dialkylthiolphosphoric acid diester-amides, for example, O,S-dimethyl-N-(methyl- and tert.-butyl-aminomethylene)-thiolphosphoric acid diester-amide, have insecticidal and acaricidal properties (see German Offenlegungsschrift (German Published Specification) No. 2,211,338).

The present invention now provides, as new compounds, the N-(aminomethylene)-(monothio and dithio)-phosphoric acid diester-amides of the general formula

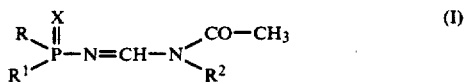

wherein
R and R$^1$, which may be identical or different, each represent alkoxy or alkylthio,
R$^2$ represents alkyl and
X represents oxygen or sulphur.

Preferably, R and R$^1$, which may be identical or different, each represent straight-chain or branched alkoxy with 1 to 6 (especially 1 to 3) carbon atoms or straight-chain or branched alkylthio with 1 to 6 (especially 1 to 4) carbon atoms, R$^2$ represents straight-chain or branched alkyl with 1 to 6 (especially 1 to 4) carbon atoms and X represents oxygen or sulphur.

Surprisingly, the N-(aminomethylene)-(monothio and dithio)-phosphoric acid diester-amides according to the invention have a better insecticidal, acaricidal and nematicidal action than the compounds of analogous structure and of the same type of action which are already known from the literature. The substances according to the present invention thus represent a true enrichment of the art.

The invention also provides a process for the preparation of an N-(aminomethylene)-(monothio or dithio)-phosphoric acid diester-amide (I) in which an N-(monoalkylaminomethylene)-(monothio or dithio)-phosphoric acid diester-amide of the general formula

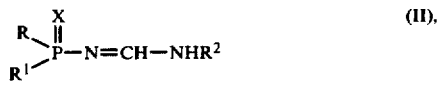

in which
R, R$^1$, R$^2$ and X have the meanings stated above, is reacted with acetic anhydride, optionally in the presence of an organic solvent.

If, for example, O,S-dimethyl-N-(tert.-butylaminomethylene)-thiophosphoric acid diester-amide and acetic anhydride are used, the course of the reaction can be represented by the following equation:

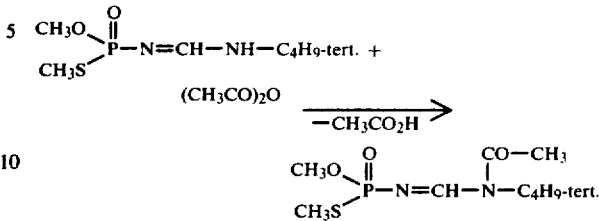

The N-(Monoalkylaminomethylene)-(monothio or dithio)phosphoric acid diester-amides to be used as starting materials are known (see German Offenlegungsschrift (German Published Specification) No. 2,211,338); they can all be prepared by processes which are known from the literature from the corresponding known N-(alkoxymethylene)-(monothio or dithio)-phosphoric acid diester amides (see (German Offenlegungsschrift (German Published Specification) No. 2,517,101) and monoalkylamines. Examples of these starting materials are: O,S-dimethyl-, O,S-diethyl-, O,S-di-n-propyl-, O,S-di-iso-propyl-, O-methyl-S-ethyl-, O-methyl-S-n-propyl-, O-methyl-S-iso-propyl-, O-methyl-S-n-butyl-, O-methyl-S-iso-butyl-, O-methyl-S-sec.-butyl-, O-methyl-S-tert.-butyl-, O-ethyl-S-n-propyl-, O-ethyl-S-isopropyl-, O-ethyl-S-n-butyl-, O-ethyl-S-iso-butyl-, O-ethyl-S-sec.-butyl-, O-ethyl-S-tert.-butyl-, O-n-propyl-S-ethyl-, O-n-propyl-S-iso-propyl-, O-n-propyl-S-n-butyl-, O-n-propyl-S-iso-butyl-, O-n-propyl-S-sec.-butyl-, O-n-propyl-S-tert.-butyl-, O-iso-propyl-S-ethyl-, O-iso-propyl-S-n-propyl-, O-iso-propyl-S-n-butyl-, O-iso-propyl-S-sec.-butyl-, O-iso-propyl-S-iso-butyl- and O-iso-propyl-S-tert.-butyl-N-(methylaminomethylene)- and -N-(ethylaminomethylene)-, -N-(n-propylaminomethylene)-, -N-(isopropylaminomethylene)- and -N-(n-butylaminomethylene)-thiolphosphoric acid diester-amide and the corresponding thiono analogues; O,O-dimethyl-, O,O-diethyl-, O,O-di-n-propyl- and O,O-di-iso-propyl-N-(methylaminomethylene)- and -N-(ethylaminomethylene)-, -N-(n-propylaminomethylene)-, -N-(isopropylaminomethylene)- and -N-(n-butylaminomethylene)phosphoric acid diester-amide and the corresponding thiono analogues; and S,S-dimethyl-, S,S-diethyl-, S,S-di-n-propyl- and S,S-di-iso-propyl-N-(methylaminomethylene)- and -N-(ethylaminomethylene)-, -N-(n-propylaminomethylene)-, -N-(isopropylaminomethylene)- and -N-(n-butylaminomethylene)- phosphoric acid diester-amide.

The acetic anhydride which is also to be used as a starting material is known and can also be easily prepared on a large industrial scale.

The process for the preparation of the compounds according to the invention is preferably carried out in excess acetic anhydride, this functioning as the reactant and, at the same time, as the solvent.

The reaction temperature can be varied within a relatively wide range. In general, the reaction is carried out at from 40° to 100° C., preferably at from 55° to 75° C.

In general, the reaction is allowed to proceed under normal pressure.

In the preferred manner of carrying out the process, the acetic anhydride is employed in excess, and the mixture of the phosphoric acid ester-amide and acetic anhydride is heated for several hours. Thereafter, the reaction mixture is dissolved in an organic solvent, for example toluene. In order to remove the acetic acid formed, the organic phase is washed with water and then with a bicarbonate solution. The solvent is stripped off in vacuo.

The new compounds are obtained in the form of oils, some of which cannot be distilled without decomposition, but can be freed from the last volatile constituents by socalled "incipient distillation," that is to say by prolonged heating to moderately elevated temperatures under reduced pressure, and can be purified in this manner. The refractive index is used for their characterization.

The active compounds are well tolerated by plants, have a favorable level of toxicity to warm-blooded animals, and can be used for combating arthropod pests, especially insects or acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for exaple *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperture and under normal pressure, for example aerosol propellants, such as halogenated hydrocarbons as well as butane, propane, nitrogen and carbon dioxide.

As solid carriers there may be used ground natural minerals, such as kaolines, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The compounds according to the present invention can also be used in the field of veterinary medicine.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The following example illustrates preparation of the novel compounds:

EXAMPLE 1

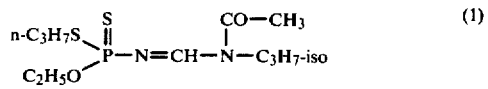

A mixture of 27 g (0.1 mol) of O-ethyl-S-n-propyl-N-(iso-propylaminoethylene)-dithiophosphoric acid diesteramide and 12 g of acetic anhydride was heated to 70° C. for 6 hours, while stirring. The reaction mixture was dissolved in 300 ml of toluene, the toluene solution was washed twice with water and once with a bicarbonate solution. The solvent was stripped off in vacuo and the residue was subjected to incipient distillation using a mercury pump. 24 g (77% of theory) of O-ethyl-S-n-propyl-N-(N'-acetyl-N'-iso-propylaminomethylene)-dithiophosphoric acid diesteramide having a refractive index $n_D^{22}$ of 1.5372 were obtained.

The following compounds of the formula

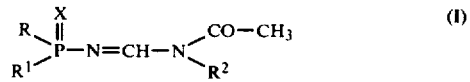

could be prepared analogously:

TABLE 1

| Compound No. | R | R$^1$ | R$^2$ | X | Refractive index: |
|---|---|---|---|---|---|
| 2 | CH$_3$S | CH$_3$O | CH$_3$ | O | $n_D^{22}$:1.5189 |
| 3 | n-C$_3$H$_7$S | C$_2$H$_5$O | CH$_3$ | S | $n_D^{21.5}$:1.5551 |

TABLE 1-continued

| Compound No. | R | R¹ | R² | X | Refractive index: |
|---|---|---|---|---|---|
| 4 | $C_2H_5O$ | $C_2H_5O$ | $C_3H_7$-iso | O | $n_D^{22}$:1.4632 |
| 5 | $C_2H_5O$ | $C_2H_5O$ | $CH_3$ | O | $n_D^{22}$:1.4620 |
| 6 | $C_2H_5O$ | $C_2H_5O$ | $CH_3$ | S | $n_D^{26}$:1.5118 |
| 7 | $C_2H_5O$ | $C_2H_5O$ | $C_3H_7$-iso | S | $n_D^{22}$:1.5039 |
| 8 | $n$-$C_3H_7S$ | $C_2H_5O$ | $C_3H_7$-iso | O | $n_D^{21}$:1.4969 |
| 9 | $n$-$C_3H_7S$ | $C_2H_5O$ | $CH_3$ | O | $n_D^{26}$:1.4902 |
| 10 | $n$-$C_3H_7S$ | $n$-$C_3H_7S$ | $CH_3$ | O | $n_D^{22}$:1.5209 |
| 11 | $n$-$C_3H_7S$ | $n$-$C_3H_7S$ | $C_3H_7$-iso | O | $n_D^{22}$:1.5104 |
| 12 | $n$-$C_3H_7S$ | $CH_3O$ | $C_3H_7$-iso | S | $n_D^{22}$:1.5463 |

The N-(monoalkylaminomethylene)-(monothio and dithio)-phosphoric acid diester-amides (II) to be used as starting materials were prepared as follows:

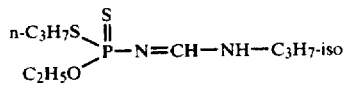

256 g (1 mol) of O-ethyl-S-n-propyl-N-(ethoxymethylene)-dithiophosphoric acid diester-amide was added dropwise to a well-stirred and cooled mixture of 700 ml of acetonitrile and 100 g of 70% strength aqueous isopropylamine solution at −5° to 0° C. in the course of 1 hour and the reaction mixture was further stirred for 2 hours and diluted with one liter of toluene. The organic phase was dried over sodium sulphate, the solvent was then stripped off in vacuo and the residue was subjected to incipient distillation using a mercury pump. 240 g (89% of theory) of O-ethyl-S-n-propyl-N-(iso-propylaminomethylene)-dithiophosphoric acid di-ester-amide having a refractive index $n_D^{23}$ of 1.5426 were obtained.

The insecticidal, acaricidal and nematicidal activity of the compounds of this invention is illustrated by the following examples wherein the compounds according to the present invention are each identified by the number (given in brackets) from Example 1.

The known comparison compounds are identified as follows:

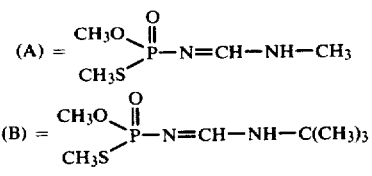

EXAMPLE 2

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dripping wet and were then infested with mustard beetle larvae (Phaedon cochleariae).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

TABLE 2

(Insects which damage plants)
Phaedon larvae test

| Active compounds | Active compound concentration in % | Degree of destruction in % after 3 days |
|---|---|---|
| (A) | 0.1 | 100 |
|  | 0.01 | 0 |
| (2) | 0.1 | 100 |
|  | 0.01 | 100 |
| (3) | 0.1 | 100 |
|  | 0.01 | 100 |
| (9) | 0.1 | 100 |
|  | 0.01 | 100 |
| (12) | 0.1 | 100 |
|  | 0.01 | 100 |
| (1) | 0.1 | 100 |
|  | 0.01 | 100 |
| (8) | 0.1 | 100 |
|  | 0.01 | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus urticae) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 3

(Mites which damage plants)
Tetranychus test (resistant)

| Active compounds | Active compound concentration in % | Degree of destruction in % after 2 days |
|---|---|---|
| (A) | 0.1 | 98 |
|  | 0.01 | 0 |
| (3) | 0.1 | 100 |
|  | 0.01 | 98 |
| (9) | 0.1 | 100 |
|  | 0.01 | 100 |
| (12) | 0.1 | 100 |
|  | 0.01 | 100 |
| (1) | 0.1 | 100 |
|  | 0.01 | 98 |
| (8) | 0.1 | 100 |
|  | 0.01 | 99 |

EXAMPLE 4

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead larvae. The root-systemic action of the active compound was deduced from the destruction data. It was 100% when all of the test larvae had been killed and 0% when just as many test larvae were still alive as in the case of the untreated control.

The active compounds, the amounts used and the results can be seen from the following table:

TABLE 4

| (Root-systemic action) | |
|---|---|
| *Phaedon cochleariae* larvae | |
| Active compounds | Degree of destruction in % at an active compound concentration of 1.25 ppm |
| (A) | 0 |
| (3) | 100 |

EXAMPLE 5

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

TABLE 5

| (Nematicides) | |
|---|---|
| *Meloidogyne incognita* | |
| Active compounds | Degree of destruction in % at an active compound concentration of 1.25 ppm |
| (B) | 0 |
| (A) | 0 |
| (3) | 100 |

It will be appreciated that the instant specification and examples are set forth by way of illustration and not limitation, and that various modifications and changes may be made without departing from the spirit and scope of the present invention.

What is claimed is:

1. An N-(aminomethylene)-(monothio and dithio)-phosphoric acid diester-amide of the formula

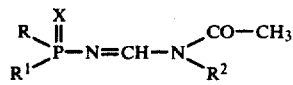

wherein
R and R¹ each independently is alkoxy or alkylthio,
R² is alkyl, and
X is oxygen or sulphur.

2. A method of combating arthropods or nematodes which comprises applying to the arthropods or nematodes, or to a habitat thereof, an arthropodicially or nematicidally effective amount of a compound according to claim 1.

3. A compound according to claim 1, wherein
R and R¹ each independently is alkoxy with 1 to 6 carbon atoms or alkylthio with 1 to 6 carbon atoms, and
R² is alkyl with 1 to 6 carbon atoms.

4. A compound according to claim 1, wherein such compound is O,S-dimethyl-N-(N'-acetyl-N'-methylaminomethylene)-thiophosphoric acid diester-amide of the formula

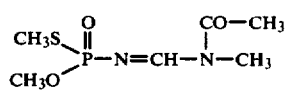

5. A compound according to claim 1, wherein such compound is O-ethyl-S-n-propyl-N-(N'-acetyl-N'-methylaminomethylene)-dithiophosphoric acid diester-amide of the formula

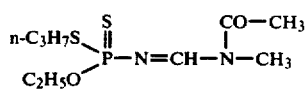

6. A compound according to claim 1, wherein such compound is O-ethyl-S-n-propyl-N-(N'-acetyl-N'-isopropylaminomethylene)-thiophosphoric acid diester-amide of the formula

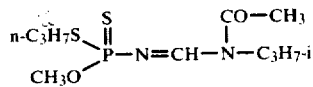

7. A compound according to claim 1, wherein such compound is O-ethyl-S-n-propyl-N-(N'-acetyl-N'-methylaminomethylene)-thiophosphoric acid diester-amide of the formula

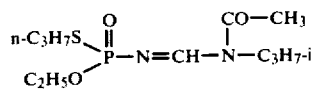

8. A compound according to claim 1, wherein such compound is O-methyl-S-n-propyl-N-(N'-acetyl-N'-isopropylaminomethylene)-dithiophosphoric acid diester-amide of the formula

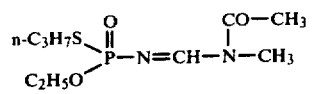

9. An arthropodicidal or nematicidal composition containing as active ingredient an arthropodicidally or nematicidally effective amount of a compound according to claim 1 in admixture with a diluent.

10. The method according to claim 2, in which said compound is
O,S-dimethyl-N-(N'-acetyl-N'-methylaminomethylene)-thiophosphoric acid diester-amide,
O-ethyl-S-n-propyl-N-(N'-acetyl-N'-methylaminomethylene)-dithio-phosphoric acid diester-amide,
O-ethyl-S-n-propyl-N-(N'-acetyl-N'-isopropylaminomethylene)-thiophosphoric acid diester-amide,
O-ethyl-S-n-propyl-N-(N'-acetyl-N'-methylaminomethylene)-thiophosphoric acid diester-amide or
O-methyl-S-n-propyl-N-(N'-acetyl-N'-isopropylaminomethylene)-dithio-phosphoric acid diester-amide.

* * * * *